US007022682B2

(12) United States Patent
Daniels (10) Patent No.: US 7,022,682 B2
(45) Date of Patent: Apr. 4, 2006

(54) METHOD FOR THE TREATMENT OF DIABETES

(75) Inventor: Bruce Alan Daniels, Oklahoma City, OK (US)

(73) Assignee: Endomatrix, Inc., Santarosa, CA (US)

( * ) Notice: Subject to any disclaimer, the term of this patent is extended or adjusted under 35 U.S.C. 154(b) by 86 days.

(21) Appl. No.: 10/438,088

(22) Filed: May 14, 2003

(65) Prior Publication Data

US 2004/0116378 A1 Jun. 17, 2004

Related U.S. Application Data

(63) Continuation-in-part of application No. 10/320,309, filed on Dec. 16, 2002, now Pat. No. 6,797,705.

(51) Int. Cl.
*A61K 31/715* (2006.01)
(52) U.S. Cl. .................... 514/53; 514/54; 514/866; 536/122
(58) Field of Classification Search ............... 514/53, 514/54, 866; 536/122
See application file for complete search history.

(56) References Cited

U.S. PATENT DOCUMENTS

| 4,758,283 A | 7/1988 | Takemura |
| 5,268,366 A | 12/1993 | Maeda |
| 5,321,133 A | 6/1994 | Colliec |
| 5,698,534 A | 12/1997 | Nagaoka |
| 5,948,405 A | 9/1999 | Cedro |

FOREIGN PATENT DOCUMENTS

JP 411080003 A * 3/1999

OTHER PUBLICATIONS

Tanner, Felix C. , "Oxidized Low Density Lipoproteins inhibit Relaxations of Porcine Coronary Arteries" Circulation vol. 83, No. 6 Jun. 1991 pp. 2012-2020.

Kim, HH, etaaal. "Basic peptide system for efficient delivery of foreign genes" *Biochim Biophys Acta* May 12, 2003, 1640 (2-3) pp. 129-136.

Hiraoka, Atsushi . "Capillary-Isotachophoretic Analyses of Algal Acidic Polysaccharides . . . " *Chem Pharm Bull* Mar. 1992. vol. 40, No. 3, pp. 783-785.

Hayakawa, Yumiko. Et al. "Inhibition of Thrombin by Sulfated polysaccharides isolated from Green Algae" Biochim Biophys Acta (1543 (2000) pp. 86-94.

(Continued)

*Primary Examiner*—James O. Wilson
*Assistant Examiner*—Everett White
(74) *Attorney, Agent, or Firm*—Ali Kamarei, Esq.

(57) ABSTRACT

The present invention provides for a method for treatment and prevention of Type II Diabetes Mellitus and its complications comprising the step of administering to a patient a therapeutically-effective amount of Rhamnan Sulphate, its functional analogs, or its physiologically acceptable salts, in therapeutic proportions. Anticoagulation activity in the blood plasma of a patient is not appreciably increased.

19 Claims, 3 Drawing Sheets

Hard Clot
Soft Clot

OTHER PUBLICATIONS

Petrie, Jr, et al. "Endothelial Nitric Oxide production and Insulin Sensitivity. " *Circulation*. Apr. 1, 1996. vol. 93, No. 7. pp. 1331-1333.

Van Den Born, J etal. "Vessel Wall heparan sulfate and transcapillary passage of albumin in experimental diabetes in thearat. " *Nephrol DialTTransplant* 1997, vol. 12 supp. 2, pp. 27-31.

Du, Xl, et al. "Hyperglycemia inhibits endothelial Nitric Oxide synthase activity by posttranslational mo Modification at the Aki site." *J Clin Invest* Nov. 2001 vol. 108, No. 9 pp. 1341-1348.

Minmin, C, etaal. Advanced Glycation end products induce apoptosis and procoagulant activity in culture human umbilical vein endothelial cells. *Diabetes Res Clin Pract*. Dec. 1999, vol. 46, No. 3 pp. 97-202.

Ebara, T, etaal . "Delayed catabolism of apoB-48 lipoproteins due to decreased heparan sulfate proteoglycan production in diabetic mice." *J. Clin Invest*. Jun. 2000 vol. 105, No. 12. pp. 1807-1818.

Raats, CJ, et al. "Glomerular heparan sulfate alternations mechanisms and relevance for proteinuria." *Kidney Int*. Feb. 2000. vol. 57. No. 2, pp. 385-4000.

Conde-Knape K. "Heparan sulfate proteoglycans in experimental models of diabetes: a role for perlecan in diabetes complications." Diabetes Metab Res Rev. Nov.-Dec. 2001, vol. 17, No. 6, pp. 412-421.

Yokoyama, H, etaal. "Serun and Urinary concentrations of heparan sulfate in patients with diabetic nephropathy" Kidney Int. Aug. 1999. vol. 56, No. 2 pp. 650-658.

Jensen, T. "Pathogenesis of diabetic vascular disease: evidence for teh role of reduced heparan sulfate proteoglycan." *Diabetes* Sep. 1997, vol. 46, supp 2 pp. S98-100.

Hayden, Melvin, et . al . Is type 2 diabetes mellitus a vascular disease with hyperglycemia a late manifestation? *Cardiovascular Diabetology*. Feb. 12, 2003. vol. 2, No. 2.

Yoyoneda, A, et al. "Regulation of cytoskeletal organization by syndecan transmembrane proteoglycans." *Matrix Biol*. Mar. 2003, vol. 22, No. 1 pp. 25-33.

Sai, P. et al. "Heparin attenuates low-dose streptozotocin-induced immune diabetes in mice and inhibits the beta-cell binding of T-splenocytes in vitro.":*Diabetologia* Apr. 1991 vol. 34. No. 4 pp. 212-217.

Moberg L, et al. "Production of tissue factor by pancreatic islet cells asaa trigger of detrimental thrombotic reactions in clinical islet transplantation." *Lanceet* Dec. 21, 2002. vol. 360, No. 9350. pp. 2039-2045.

Cnop, M, et al. "Low Density lipoprotein can cause death of islet beta-cells by its cellular uptake and oxidative modification." *Endocrinology* Sep. 2002, vol. 143, No. 9 pp. 3449-3453.

Miller, AW, et al. "Mechanisms of Impaired Endothelial Function Associated with Insulin Resistance" *J Cardiovasc Pharmacol Ther* Apr. 1998, vol. 3, No. 2 pp. 125-134.

Sadri, P, et al. "Blockade of hepatic nitric oxide synthase causes insulin resistance" *Am J Physiol* Jul. 1997 vol. 277, No. 1 pt 1, pp. 101-108.

Wascher, TC, et al. "Effects of Low-dose L-arginine on insulin mediated vasodilation and insulin sensitivity" *Eur J Clim Invest* Aug. 1997, vol. 27, No. 8, pp. 690-695.

* cited by examiner

Rham = Rhamnose residue

S = Sulfate Ester

METHOD FOR THE TREATMENT OF DIABETES

REFERENCE TO RELATED PATENT APPLICATION

Reference is made and priority is claimed to patent application Ser. No. 10/320,309, filed Dec. 16, 2002, issued Sep. 28, 2004, U.S. Pat. No. 6,797,705, entitled: "Rhamnan Sulphate Composition for treatment of Endothelial Dysfunction" by the present inventor.

FIELD

This invention relates to a pharmacological composition and method that provides for regression of neuropathies associated with but not limited to diabetes, preservation of renal function in diabetic states and other vasculopathic states. This composition is preferably used for patients susceptible to or suffering from diabetes, an endothelial dysfunction disorder or disease, and more particularly, but not by way of limitation, to a formulation with enhanced absorption characteristics for preventing and/or treating, type II diabetes mellitus, and its complications, without appreciably increasing the patient's risk of hemorrhaging, either internal or as a result of an external injury.

BACKGROUND

Type II Diabetes Mellitus and other diseases resulting from endothelial dysfunction, and their associated complications are a principal cause of disabilities and deaths of individuals in the world. For example, in recent years more than 700,000 deaths have occurred annually in the United States alone as a result of coronary artery disease, and many more patients have been hospitalized for unstable angina, acute myocardial infarction, and congestive heart failure, which occur in greater than 70% of patients with diabetes as the disease progresses. Additionally, diabetes is the most common cause of chronic renal insufficiency and renal failure in industrialized societies and a major cause of blindness and limb loss due to leg ischemia.

There has been significant and extensive research for effective long-term treatment for diabetes. However, present treatments for such disorders are partial treatments such as administration of insulin, and oral hypoglycemic agents. These treatments have serious shortcomings in long-term effectiveness. The use of these treatments does not resolve the spectrum of molecular and physiologic abnormalities attendant to the diabetes processes.

Diabetes is a medical condition associated with low enos activity, and high superoxide and other free radicals being generated in association with cellular hyperglycemia. These abnormalities result in alterations and defects in cellular matrix composition and cellular function in a variety of cell types including the pancreas, liver, kidneys, endothelium and cardiovascular system.

Currently available treatments have to date been only partially effective for favorable long-term results. None of these treatments have been designed to maintain, improve, or restores cellular function of the cell matrix of these cited organs and tissues by impacting the cell matrix and control of the generation of nitric oxide, superoxide, and other free radicals.

The focus of current treatment methods is to react to potentially immediate danger to one's life. These treatments and their shortcomings include;

Insulin injections: Shortcoming: hypoglycemia, inconvenience, and discomfort of administration.

Diet: Shortcoming: hard to follow.

Oral Medication: Metformin, Glucophage, Shortcoming: for severe hyperglycemia it is insufficient and does not treat the other dysmetabolic effects of the disease.

Kidney-Pancreas transplant: Shortcoming: Can't find donors.

None of these treatment methods is directed towards the underlying disease processes, the molecular causes of the disease or disorders, the effects of the hyperglycemia on the basal molecular organization and properties of the cells, or towards restoring the structure and function of the blood vessels and other cell types to levels that reduce or eliminate the danger posed by diabetes. There is no treatment designed to reduce the level of free radical generation, of cell matrix re-organization, cell membrane composition, of clotting activity or preservation of vascular thromboresistance.

In view of the foregoing, there is a significant need for a pharmacological composition and method that is directed towards treating the underlying diabetes disease process, and towards preserving and restoring the structure and improving the functions of the various cell types involved with the diabetic processes and in particular the function-structure properties of the endothelium which lines the entire cardiovascular system and which is the interface of the blood with the vascular system and a major determinant of effective renal function.

It is an objective of the present invention to provide a treatment, which is directed to preventing and minimizing dysfunctional atomic and molecular interactions within the human cellular matrix or cellular environment, which lead to diabetes.

It is another objective of the present invention to provide a treatment that is directed to retarding adverse consequences of free radicals generated in human cellular matrix. It is also another objective of the present invention to stimulate an increased production of nitric oxide within human cellular matrix or cellular environment and to decrease production and effects of superoxide and other free radicals throughout the course of the disease.

It is yet another objective of the present invention treatment of cardiovascular diseases, in particular cell surface based thrombosis, without appreciably increasing blood anticoagulation activity in patients.

SUMMARY

The present invention provides for a method for treatment of Type II Diabetes Mellitus and its complications comprising the step of administering to a patient a therapeutically-effective amount of Rhamnan Sulphate, its functional analogs, or its physiologically acceptable salts, in therapeutic proportions. The anticoagulation activity in the blood plasma of a patient is not appreciably increased. The Rhamnan Sulphate is extracted from algae. Preferably the algae are either Monostroma Nitidum or Monostroma Latissimum. As another option, the method comprises the co-administration of L-Arginine and Rhamnan Sulphate.

The present invention also provides a method of improving the structural integrity of islet cells for the treatment of Diabetes comprising the step of administering to a patient an effective amount of Rhamnan Sulphate, its functional analog, or its physiologically acceptable salts, as known in this industry. The improved islet cells prevent the onset of Type II Diabetes, neuropathy, nephropathy, arteriosclerosis, or proteinuria. Further, the improved islet cells prevent the onset of thrombogenic activity.

The method of this invention aids in treatment of the mammalian cellular environment for the treatment of endothelial dysfunction caused by Type II Diabetes or its complications, comprising of Rhamnan Sulphate, its functional analog, or its physiologically acceptable salts in therapeutic proportions. The composition of Rhamnan Sulphate and L-Arginine are formed into a Rhamnan Sulphate—L-Arginine complex by covalent bonding. It is understood that composition optionally comprises a mixture of functional analogs or physiologically acceptable salts of Rhamnan Sulphate.

One advantage of the method and composition of the invention is that it possesses extremely potent cell surface and matrix antithrombotic activity and other effects, which lead to, increased enos activity and reduced free radical damage to cells and tissues affected by diabetes.

Another advantage of the described composition is that there is less peptide residual in extracting the composition from plant cells as compared to heparin from animal cells. Hence, it is less allergic reaction prone and has fewer immunogenic properties.

Yet another advantage is that since Rhamnan Sulphate is from plant cells, it has no potential for the transmission of potentially lethal and serious prion diseases such as mad cow disease.

Another advantage is that Rhamnan Sulphate has no potential for activating Platelet Factor IV and resulting in immune complex destruction of platelets as seen with heparin administration.

Finally, another advantage of Rhamnan Sulphate is that it is a functional substitute for heparin in applications requiring systemic anticoagulant activity such as dialysis, bypass surgery, and polymer tube coatings and devices for use in mammals and humans.

DETAILED DESCRIPTION

As has been previously described it is a conception of the inventor that a cellular environment (cellular matrix or gel matrix) composed of charged polymers-highly charged peptide-water polymers, such as heparin-arginine-water is responsible for controlling the structure and ultimately the function of human cells within this cellular environment. This charged polymer-arginine-water environment impacts such important functions of the cells by effecting protein distribution and functionality, cell signaling processes, genetic or DNA-RNA transcription regulation, and the physical/chemical properties of cells, including blood vessel wall cells. The inventor, in U.S. Pat. Nos. 6,255,296 and 6,495,530, outlines the fact that a disruption in the structure of the cellular environment, and in particular the endothelial cells, is the proximate cause of diseases such as cardiovascular disease. The specifications of those patents are hereby incorporated by reference herein. While not bound to a particular mechanism of operation, the inventor's conception is that the loss of heparin sulfate causes a reduction in Nitric Oxide formation.

It should be noted that heparins or heparin domains within these polymer structures are members of the group commonly referred to as endogenous heparans. Exogenous heparans, including heparin, have functions, which protect the endogenous heparans.

The present invention is directed to a formulation for treatment of the gel matrix or cellular environment for treatment of endothelial dysfunction and inhibiting Type II Diabetes, and related diseases or complications such as neuropathy, nephropathy, and proteinuria. In accordance with the invention, a patient susceptible to or suffering from Type II Diabetes, or other diseases associated with Type II Diabetes, is treated with a therapeutically effective amount of a substance characterized as Rhamnan Sulphate or its functional analogs or physiologically acceptable salts.

A therapeutically effective amount of Rhamnan Sulphate is defined primarily by clinical response in a patient, and ranges from about an equivalent of 2,000 IU to 200,000 IU of heparin daily on variable schedule. A more preferred range of an effective amount of Rhamnan Sulphate is between about an equivalent of 5,000 to 20,000 IU of heparin daily on a variable schedule of heparin. A most preferred range of an effective amount of Rhamnan Sulphate is between about an equivalent of 8,000 IU and 12,000 IU of heparin daily on variable schedule of heparin. Preferably the dose of Rhamnan Sulphate is repeated daily to achieve the desired effect.

When absorbed into the charged polymer-highly charged peptide-water matrix, Rhamnan Sulphate protects and reinforces structure and roles of endogenous heparin. Whatever the mechanism, Rhamnan Sulphate absorption has a potent effect on treatment of the endothelium.

For example, the Rhamnan Sulphate is characterized such that it should be an amount sufficient to exert cell surface anti-thrombotic effects on the endothelial cells, while not increasing the patient's risk of internal or external hemorrhaging and effectively maintaining integrity and functionality of the cellular membranes and surrounding environments of the endothelial cells.

Again, effective doses of Rhamnan Sulphate vary with the particular patient condition and the method of administration. For example, it is noticed that subcutaneous injection of heparin results in greater concentration in the cellular and membrane domains than intravenous injection, and it is the inventor's observation that oral heparan sulphates localizes almost exclusively to cell surface membranes, especially the endothelium. Thus, the preferred method of administration of Rhamnan Sulphate for the present invention is through the oral route, while the least preferred method is via intravenous injection.

The compound of the present invention is preferably formulated for oral, sublingual, subcutaneous, intravenous, transdermal or rectal administrations in dosages and in admixture with pharmaceutical excipients or vehicles including implantation or controlled-release devices. For example, the compound of Rhamnan Sulphate can be dispersed in a physiologically acceptable, non-toxic liquid vehicle, such as water.

Furthermore, the compound of the present invention is optionally used, either alone or in conjunction with other material that are currently used as capsules, to form a capsule shell. The capsule shell comprised of the compound of the present invention is then used to administer or deliver other pharmaceuticals, nutrients, or vitamins and minerals.

Alternatively, the compound can be given in tablet, capsule, powder, granules, coated tablet form, or mixed with various food items such as cereals, bread, drinks, health bars, or other functional foods. The compound is made using conventional methods, and may be mixed with conventional pharmaceutical auxiliaries, such as binders, fillers, preservatives, tablet disintegrators, flow regulators, plasticizers, wetting agents, dispersants, emulsifiers, solvents, retarding agents and/or anti-oxidants. It is also optionally contained or formed into a complex with lipids in various formulations and molecular arrangements.

The inventor recognizes as integral to the invention, that the Rhamnan Sulfate administered orally has no or insignificant plasma anti-coagulation activity. The invention achieves treatment of the endothelium and Diabetes without the inhibition of plasma anticoagulant factors. Thus, the invention avoids the risks of spontaneous hemorrhage or excessive bleeding due to vessel injury attendant to plasma anticoagulation with currently available anticoagulant treatments such as Coumadin® and heparin.

Localization of administered heparin or heparin analogues to cell surfaces (e.g. endothelial surfaces) by oral administration inhibits thrombotic activity within and on artery and blood vessel surfaces without the inhibition of plasma clotting factors seen with currently available anticoagulants.

An efficiently operating homeostatic system is crucial to cellular function within mammalian organisms. In a healthy state, there is formed a gel matrix of heparin, highly charged peptide and water polymers, which houses a plurality of other molecules by accommodating dynamic binding of and release of such molecules without reaching concentration levels which destroy the gel structure and its regulatory functionalities.

Rhamnan Sulphate is derived from plant sources such as algae. Typical plant sources of Rhamnan Sulphate and Rhamnan Sulphate analogs include, Monostroma Nitidum and Monostroma Latissimum. Such plants are considered to be an effective and efficient source of Rhamnan Sulphate compounds for use in the present invention.

Long chain charged polymer strands are an organizing determinant for membranes, proteins, receptors, ion channels, cell organelles, nuclear membranes, membrane pores, and other complex cellular constituents. The polymers and highly charged amino acids such as Arginine organize water into arenas for confining bilipid layer membranes, for example, creating cell turgor and form and limiting hydrolytic properties of water on other molecular structures.

Rhamnan Sulphate's high sulphate content imparts a high negative charge which attracts and binds positively charged substances like basic amino acids, basic domains of proteins and peptides, cations, water and other such charged molecules. Arginine has a high positive charge and strongly associates with heparin along membrane surfaces such as endothelium and basement membranes an in association with water, organize as gel matrix.

The gel may be in a constant state of change, including transitions from one state or phase to another. As such, conformation can change and derangements occur as different substances move in and out of the gel matrix and as the gel properties change.

A healthy gel matrix is formed from endogenous charged polymers, endogenous arginine and water. An unhealthy state of a gel matrix has some of the highly charged peptides molecules cleaved out of the gel. Likewise, charged polymers have been removed from the gel. There are thus created gaps between charged polymers into which other molecules can embed or pass through.

The healthy gel structure has a conformation that preferentially supports interaction and binding of foreign molecules. The capacity to accommodate intrusions of such molecules before the gel structure collapses and loses its functionality is an important characteristic of the gel system.

An example of polar molecules that heparin binds and inactivates, thereby modulating their activity, are serine proteases, other clotting factors and thrombolytic agents, antithrombin-thrombin, complement, apo-lipoproteins, growth-promoting factors, mitogens, heparinase, lipoprotein lipase, growth-inhibiting factors, chemotactic factors, super oxide dismutase, cytokines, numerous enzymes, and cytoskeletal proteins such as fibronectin.

As these intrusions accumulate locally or in a distributed fashion, they cause interference within the gellular association of charged polymers and highly charged peptide. The interference can cause the gel structure to deteriorate, thus increasing its porosity or collapse altogether in a localized or distributed fashion. In addition, the intrusion may trigger a release of other bound polar molecules, such as calcium, which would induce a non-homeostatic event.

The permeability created by the interference of such molecules allows macromolecules or cells to enter and traverse the gel. For example, cholesterol, clotting factors and water traverse the gel reaching a bilipid layer, or other subendothelial locations. In addition, ionic strength, flow stress, heat, osmotic pressure or other forms of energy transfer to the gel can deteriorate the properties of the gel as described above.

These intrusions result in a displacement of arginine and decreased generation of nitric oxide as an additional effect. Intrusions limit the binding capacity of the heparin for arginine and other molecules within the gel.

Further, while not being bound to a mechanism of operation, LDL receptors on pancreatic islet cells take up LDL, which leads to inflammation and tissue factor production (analogous to plaque in arteries). Rhamnan Sulfate is believed to suppress both the inflammation and tissue factor-induced coagulation in pancreatic cell membranes and cell matrix just as it does in endothelial and artery cell matrix. Rhamnan Sulphate therefore prevents the progressive islet cell damage and insulinopenia associated with Type I and Type II diabetes.

In order to reverse this disruption of the gel matrix caused by the removal of arginine and/or heparin, the present invention employs Rhamnan Sulphate to maintain and rejuvenate the islet cells, gel matrix and their functionality. In this regard, the present invention utilizes Rhamnan Sulphate to give optimal pore closure and stabilization, and number and distribution of binding sites, wherein signaling, anti-proliferation, cell surface anti-thrombotic, and anti-inflammatory effects are maintained. Thus, the homeostasis-promoting functionalities of heparin, arginine, and charged polymer-highly charged peptide-water gel matrix, resultant from the herein-described composition, retard continuous and accumulative change and injury to cellular domains. By this retarding effect, cholesterol accumulations generally referred to as "arterial plaques" are minimized.

Similar cell matrix and membrane changes in pancreatic cells and kidney cells are recognized to occur and to cause an inflammatory activity analogous to those seen in atherosclerotic plaque formation.

Addition of Rhamnan Sulphate to the gel system protects the functionality of both heparin and the arginine in the gel matrix. In the extragellular medium, the ability of heparin to bind and quiesce molecules is augmented by simultaneous addition of Rhamnan Sulphate, wherein Rhamnan Sulphate binds to extragellular potentially-intruding molecules, thus allowing existing gellular charged polymers to associate with gellular arginine.

Nitric oxide produced from arginine is an important physiological mediator. The enzyme responsible for nitric oxide production, nitric oxide synthase, requires CA++ and Calmodulin. The functionality of the heparin-arginine gel includes its binding and regulation of CA++ and Calmodulin. By regulating Calmodulin activity, the effects of Rhamnan Sulphate on the charged polymer-arginine gel regulates nitric oxide synthase activity responsible for nitric oxide production.

The binding of water, small anions and cations within the charged polymer-arginine-water gel is facilitated by pi-bonding properties inherent in the saccharide ring structure within the charged polymers. Changes in the shared electron density and electrical charge variation regulated the state of solvation and conformation of the gel polymers. Thus, small anion and cation binding induces changes in the state of salvation, changes in catalytic and hydrolytic properties of water, and changes in capacity of the gel to bind water and other molecules. Low to high molecular weight Rhamnan Sulphate, preferably having a high degree of sulfation, is preferably used.

Endothelial cell injury and pancreatic cell injury occur from free radicals. Heparin binds super oxide dismutase, which absorbs high-energy electrons and deactivates free radicals. Rhamnan Sulphate, heparin, and nitric oxide bind free radicals preventing damages to multiple cell types including pancreatic cells and endothelial cells.

Type II Diabetes is in part due to free radical injury to pancreatic cells. Rhamnan Sulphate, heparin, super oxide dismutase and nitric oxide all attack and neutralize free radicals, therefore, diseases associated with cellular injury from free radicals are effectively treated and prevented by the present invention. Also, Rhamnan Sulphate aids in the reconstruction of damaged tissue by promoting the production of endogenous heparin, which then forms a complex with and removes extra cellular matrix protein accumulations, e.g. fibronectin with consequent reversal or minimization of organ hypertrophy states. Rhamnan Sulphate enhances regeneration of endothelium following an injury to an endothelium surface.

EXAMPLE 1

Dried green Algae (Monostroma Nitidum) were swollen in 10 Vols. of water at room temperature for one hour. Thereafter the swollen green algae was ground and refluxed for two (2) hours in a boiling water bath. The water extract was centrifuged (4500 g) for 30 minutes, and the water-soluble polysaccharide in the non-dialyzable fraction was obtained by lyophilization.

The crude polysaccharide was dissolved in water and was applied to a column (2.4×100 cm) of DEAE-cellulose (Whatman DE-52). Starch or neutral polysaccharides were removed by continuous water elution until the sample was completely free as determined by phenol-sulfuric acid detection. Afterwards, acid polysaccharide was fractionated by stepwise alteration of the ionic strength of KCL at 0.5. 0.7 and 2.0 M, and then each fraction were desalted and freeze dried. The 0.5 M KCL fraction (major fraction) successive purification procedures were performed by gel filtration chromatography on a Toyopearl HW-65 (fine) column (1.2× 100 cm). The sample was eluted with water at a flow rate of 0.4 ml/min. The major fraction was collected and freeze dried. These procedures or variations of them for extraction of Rhamnan Sulphate is well known.

EXAMPLE 2

Rhamnan Sulphate was prepared as described in Example 1 and was tested for cell surface anti-thrombotic activity, as described below. Rhamnan sulphate was dissolved in water at concentrations 20, 10 and 5 mg/ml. For experiments utilizing L-Arginine, L-Arginine capsules were opened and contents were dissolved in water at 300 mg/ml for 4 hr studies and 150 mg/ml for the 28 day study. Rhamnan sulphate-arginine complex (RS–LR), where L-Arginine is covalently bound to Rhamnan Sulphate to form a physiologically acceptable salt of Rhamnan Sulphate, was dissolved in water at concentrations of 20, 10, 3 and 0.3 mg/ml. Bovine ung unfractionated heparin, 150 units/mg, Lot No ZX320, was obtained from Upjohn Ltd. Heparin was dissolved in water at a concentration of 20 mg/ml.

One hundred and two male Wistar rats, weighing 312±64 g (±SD), were handled and housed according to the Principles of Animal Care set out by the Canadian Federation of Biological Societies. The animals were fasted overnight prior to treatment and were anaesthetized with barbital and methoxyflurane for experimental procedures.

Rhamnan sulphate was administered to rats at 7.5, 4 and 2 mg/kg with 5, 20, and 5 rats/group respectively. Rhamnan sulphate (7.5 mg/kg) plus arginine (112.5 mg/kg) was administered to 5 rats. Rhamnan sulphate-arginine complex was administered to rats at 4, 1 and 0.1 mg/kg with 20 rats/group. The Rhamnan-arginine complex was weighed fresh daily. All of the Groups and the administered compounds are shown in Table 1. Six to 8 rats were treated per day. A stomach tube was filled with 0.2 ml saline followed by 0.09–0.18 ml of the Rhamnan Sulphate solutions or 0.1 ml of arginine solution depending on rat weight. Thus when the stomach tube was placed in the stomach the drugs were first introduced into the stomach followed by saline to give a total volume of approximately 0.4 ml. In the heparin alone group, heparin was administered in a volume of 0.1–0.2 ml followed by 0.2 ml saline. Control group was saline alone.

TABLE 1

| Group 1 | No Treatment |
| --- | --- |
| Group 2 | Heparin alone at 7.5 mg/kg |
| Group 3 | Rhamnan Sulphate alone at 7.5 mg/kg |
| Group 4 | Rhamnan Sulphate alone at 4 mg/kg |
| Group 5 | Rhamnan Sulphate alone at 2 mg/kg |
| Group 6 | Rhamnan Sulphate 7.5 mg/kg + L-Arginine 112 mg/Kg |
| Group 7 | Salt of Rhamnan Sulphate 4 mg/kg – L-Arginine |
| Group 8 | Salt of Rhamnan Sulphate 1 mg/kg – L-Arginine |
| Group 9 | Salt of Rhamnan Sulphate 0.1 mg/kg – L-Arginine |

Thrombosis Test

The thrombosis test was performed by a modification of the procedure by Blake et al. For animals exposed to treatment for 4 h, a thrombus was initiated in the right jugular vein by application of 10% formalin in 65% methanol to the exposed adventitial surface. Immediately following, drugs were introduced into the stomach by stomach tube. At 4 h after thrombus initiation animals were again deeply anaesthetized and first examined for any external signs of bleeding. The jugular vein was exposed and examined for the presence of a plug using a cotton pledget. The clot was scored as + (hard clot) if the vessel is blocked and remained blocked despite examination with a cotton pledget. The clot was scored as +/− (soft clot) if the vessel appeared completely blocked on first examination and then opened as it was examined. The thrombus was scored as − (negative) if blood was seen to flow freely in the vessel.

Collection of Blood and Blood Vessels

Immediately after examination of the jugular vein, a laparotomy was performed and a blood sample of approximately 10 ml (9 parts blood to 1 part 3.8% sodium citrate) was taken from the abdominal aorta. Plasma was prepared. As a source of endothelium, the thoracic aorta or vena cava was removed and placed in saline. Each animal was examined for signs of internal hemorrhage and the time when blood clotted in the body cavity was recorded.

Harvesting of Endothelium

Endothelium was removed from blood vessels according to the method of Hiebert and Jaques. The vessels were slit open, pinned to dental wax lumen side up, and rinsed in Locke's solution. Cellulose acetate paper was applied to the lumenal surface and when lifted, endothelium was removed. The length and width of the imprint were measured to the nearest mm.

Determination of Heparin-Like Compounds with Endothelium

Cellulose acetate paper was removed from endothelium by dissolving in cold acetone followed by centrifuging and discarding the supernatant. The precipitates were further processed by digestion with pronase (10 μl of 40 mg/ml in Tris buffer). Samples were then centrifuged at 10,000 rpm for 10 min, supernatant was collected and the precipitate washed twice with 100 uL 26.8% NaCl which was added to the supernatant. GAGs were precipitated from the supernatant with five volumes of methanol and the precipitate dried. Agarose gel electrophoresis was used to identify and measure Rhamnan Sulphate in endothelial extracts by previously published methods. The dried powders, dissolved in suitable volumes of water, were applied to agarose gel slides along with the administered Rhamnan Sulphate used as a reference. Following electrophoresis, gels were fixed in 0.1% hexadecyltrimethylammonium bromide and air dried. Slides were stained with 0.04% toluidine blue in 80% acetone and background color was removed with 1% acetic acid. Heparin was identified by electrophoretic migration as compared to reference material and amounts determined by densitometry.

Statistical Analysis

Thrombosis data is expressed as a percentage with 95% confidence intervals. $X^2$ test for differences between proportions was used to compare the total thrombotic incidence and incidence of hard clots between groups. Other data is expressed as mean±SE. A one-way ANOVA with Tukeys post hoc test was used to compare the differences between groups when plasma coagulation tests and heparin-like concentrations in urine were examined.

Thrombosis Test

Figure 1:
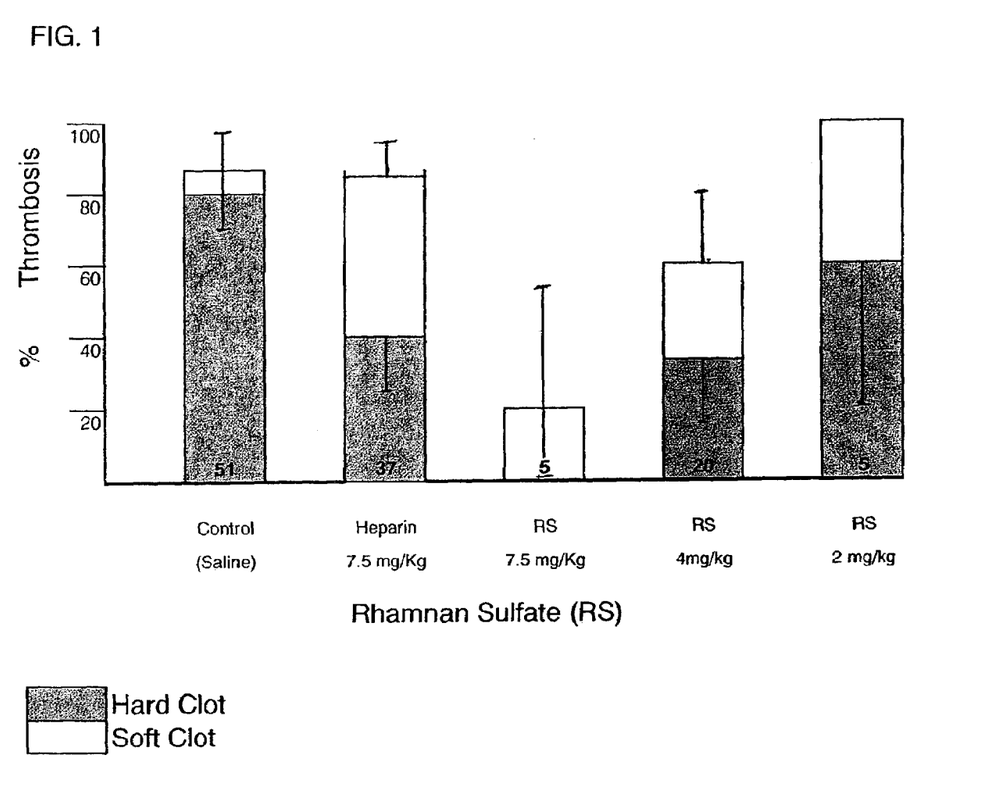
FIG. 1 is a graph comparing a control group to Heparin and groups of Rhamnan Sulphate at different dosages.

As shown in FIG. 1 an antithrombotic effect was observed with all oral doses of Rhamnan Sulphate alone, except 2 mg/kg. As well an antithrombotic effect was seen when arginine was added along with Rhamnan Sulphate or when Rhamnan Sulphate was complexed to arginine. At 2 mg/kg Rhamnan Sulphate there was a trend towards a significant reduction in hard clots versus controls although this did not reach significance. A dose response was evident with both Rhamnan Sulphate alone or when Rhamnan Sulphate was complexed to arginine. The Rhamnan Sulphate arginine complex was a significantly more effective antithrombotic agent than Rhamnan Sulphate alone as shown by a decrease in incidence of hard clots when comparing the compounds at 4 mg/kg. Further the incidence of hard clots and total thrombotic incidence was less for the Rhamnan Sulphate arginine complex at 1 mg/kg versus Rhamnan Sulphate alone at 2 mg/kg.

Figure 2:
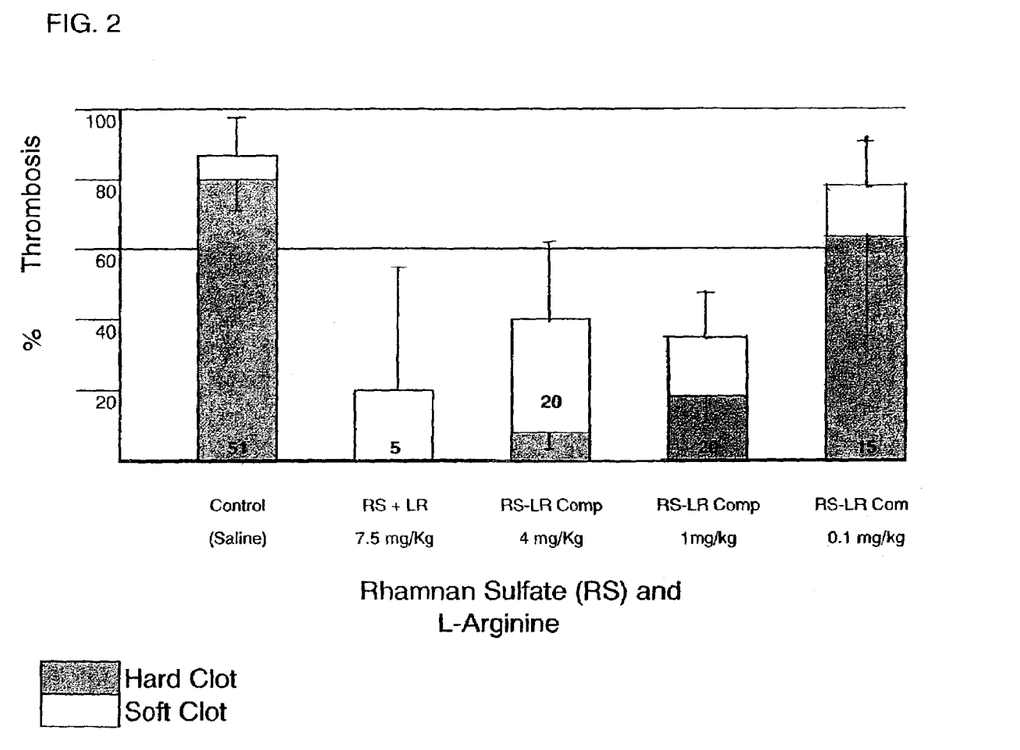
FIG. 2 is a graph comparing a control group to various groups of Rhamnan Sulphate and L-Arginine in various dosages.

FIGS. 1 and 2 show antithrombotic activity of orally administered Rhamnan Sulphate or Rhamnan Sulphate and arginine as compared to oral unfractionated heparin. Error bars show 95% confidence intervals; upward bars for total clots, downward for hard clots. RS+LR is 7.5 mg/kg Rhamnan Sulphate+112.5 mg/kg arginine); RS−LR is 7.5 mg/kg Rhamnan Sulphate arginine complex. Numbers in bars show number of rats per group.

Plasma Levels

The Rhamnan Sulphate Groups at all doses did not have a significant effect on APTT or the Heptest (Table 2). Rhamnan sulphate alone or when complexed with arginine had little or no effect on anti-Xa or anti-IIa activity. Rhamnan sulphate alone had somewhat more anti-Xa activity than the Rhamnan Sulphate-arginine complex. When anti-Xa activity was measured in the plasma of rats there was a reduced optical density in the plasma samples from some of the rats given Rhamnan Sulphate or the Rhamnan Sulphate-arginine complex. (Data not shown). There was no evidence of bleeding or blood loss in the animals.

TABLE 2

Activation partial thromboplastin time and Heptest following oral administration of Rhamnan Sulphate alone, with arginine or as a Rhamnan Sulphate-arginine complex.

|  | Dose | APTT (sec) | | Heptest (sec) | |
| --- | --- | --- | --- | --- | --- |
|  | mg/kg | Mean | SE | Mean | SE |
|  | Controls | 19.5 | 0.9 | 36.3 | 0.8 |
| Rhamnan Sulphate | 7.5 | 20.2 | 0.6 | 32.5 | 2.2 |
|  | 4 | 20.5 | 0.5 | 34.2 | 1.9 |
|  | 2 | 21.8 | 0.9 | 36.5 | 1.1 |
| Rhamnan sulphate + LR | 7.5 | 20.4 | 0.8 | 31.8 | 0.9 |
| Rhamnan Sulphate- | 4 | 22.6 | 1.5 | 36.9 | 1.0 |
| Arginine | 1 | 18.5 | 0.7 | 30.8 | 0.7 |
| Complex | 0.1 | 18.5 | 0.7 | 30.8 | 1.0 |

Rhamnan sulphate like material was also found on both aortic and vena caval endothelium. A higher concentration was found on the vena cava than on the aorta when all compounds were administered (Table 3) P<0.00003 one-tailed t-test. A dose effect was evident when venal caval concentrations of Rhamnan Sulphate were observed following Rhamnan Sulphate or Rhamnan Sulphate-arginine. A similar dose effect was seen for aortic concentrations of Rhamnan Sulphate following oral administration of Rhamnan Sulphate arginine but not Rhamnan Sulphate alone. Vena caval but not aortic concentrations were greater at 4 mg/kg for Rhamnan Sulphate but not Rhamnan Sulphate—arginine complex.

TABLE 3

|  | Dose mg/kg | Number | Aorta μg/cm$^2$ mean ± se | Vena Cava μg/cm$^2$ mean ± se |
| --- | --- | --- | --- | --- |
| Rhamnan Sulphate | 7.5 | 5 | 1.80 ± 0.79 | 11.22 ± 3.20 |
|  | 4 | 20 | 2.05 ± 0.08 | 15.97 ± 1.54* |
|  | 2 | 5 | 2.32 ± 0.33 | 3.00 ± 0.43 |

TABLE 3-continued

|  | Dose mg/kg | Number | Aorta µg/cm² mean ± se | Vena Cava µg/cm² mean ± se |
|---|---|---|---|---|
| Rhamnan sulphate + LR | 7.5 | 5 | 3.91 ± 0.65 | 7.16 ± 3.77 |
| Rhamnan Sulphate – Arginine Complex | 4 | 20 | 2.30 ± 0.07 | 4.41 ± 0.05 |
|  | 1 | 20 | 0.12 ± 0.05 | 0.42 ± 0.10 |
|  | 0.1 | 20 | 0.52 ± 0.13 | 1.89 ± 0.43 |

Rhamnan sulphate-like material found on aortic and vena caval endothelium following oral administration of Rhamnan Sulphate alone, with arginine or as a Rhamnan Sulphate – arginine complex.

Rhamnan sulphate-like material was also recovered from the urine and feces accumulated over the 4 hr period. The amounts and concentrations recovered after administration of Rhamnan Sulphate alone resulted in more being excreted in the urine than when given as a Rhamnan Sulphate-arginine complex. Amounts recovered were 3.0±0.4 and 1.6±0.4 (mean±SE) percent of dose for Rhamnan Sulphate alone versus Rhamnan Sulphate-arginine respectively.

Amounts recovered from feces also show that more is recovered when administered as Rhamnan Sulphate alone versus Rhamnan Sulphate-arginine. A dose effect was evident. Amounts recovered were 13.7±4.4 and 6.1±1.9 (mean±SE) percent of dose for Rhamnan Sulphate alone versus Rhamnan Sulphate-arginine respectively, these differences were not significant.

In general, the results indicate that Rhamnan Sulphate provides vessel surface anti-thrombotic activity without appreciably increasing plasma anticoagulation activity. Hard clots and soft clots build from the inside surface of the lumen of the injured vessel and extend radially more central into the lumen of the vessel, but there is little or no change in the plasma coagulation activity as was measured by the standard plasma coagulation tests mentioned above. Thus, Rhamnan Sulphate is effective in preventing clot formation at the inside surface of the vessel, but it does not provide the patient with increased plasma anti-coagulation activity to render the patient a "bleeder" or to be at appreciably increased risk of hemorrhaging.

The results show that without any treatment, as a control group, saline had no effect on thrombosis with approximately a 90% incidence of thrombosis of which a very high percentage were hard clots. Heparin, which is commonly used as an anticoagulant, at 7.5 mg/kg showed little or no effect in total incidence of thrombosis, however it reduced the percentage of incidence of hard clots. Conversely, Rhamnan Sulphate at the same 7.5 mg/kg dosage showed a significant decrease in incidence of thrombosis with little or no hard clots. Reduction of the dosage of Rhamnan Sulphate to 4 mg/kg and 2 mg/kg resulted in the increase in incidence of thrombosis and in the re-appearance of hard clots from the 7.5 mg/kg dose.

Figure 3:
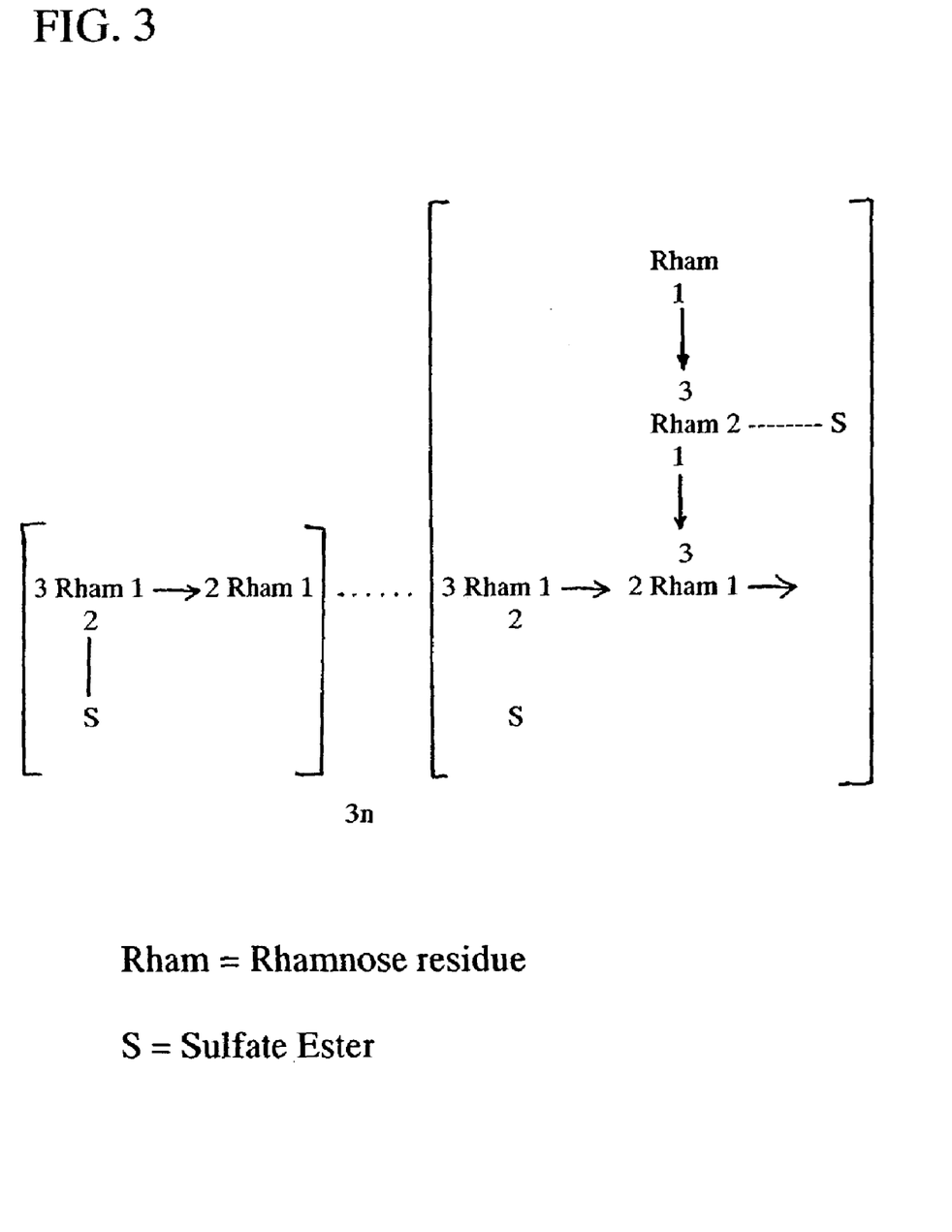
FIG. 3 is a chemical representation of the salt of Rhamnan Sulphate compound.

FIG. 2 again compares the control group with the co-administration of Rhamnan Sulphate with L-Arginine, the structure of which is commonly known. RS+LR refers to the co-administration of Rhamnan Sulphate, whereas RS–LR refers to the salt of Rhamnan Sulphate with arginine as a compound, the chemical structure of which is shown in FIG. 3. Group 6, RS+LR at 7.5 mg/kg, showed little difference with administration of Rhamnan Sulphate by itself both in the incidence of thrombosis and in the non-occurring of hard clots. Group 7, RS-LR compound at 4 mg/kg, however, showed a significant reduction in the total incidence of thrombosis from 4 mg/kg of Rhamnan Sulphate alone and a reduction in hard clots. Even Group 8, LS-LR compound at 1 mg/kg showed a slight decrease in incidence of thrombosis than and hard clots than 4 mg/kg of Rhamnan Sulphate.

The result is that Rhamnan Sulphate by itself is more effective than Heparin in lowering the incidence of thrombosis and in reducing the number of hard clots. Further, that the blood anticoagulation activity is not appreciably increased. This further desired effect is opposite that of Heparin, which is known to increase plasma anticoagulation activity. Thus, the use of Rhamnan Sulphate in treatment of endothelial dysfunction, particularly cardiovascular disease, and more particularly atheresclerosis and arteriosclerosis is desired. A second result is that the salt of Rhamnan Sulphate-arginine compound is more effective in lowering the incidence of thrombosis and hard clots than an equivalent dose of Rhamnan Sulphate alone.

It is therefore evident how the objective of the present invention is satisfied. First the method and composition of the invention possesses extremely potent antithrombotic activity and other inhibitory effects on cell surface coagulation assembly and activity for thrombus inhibition. It is well understood that accelerated cardiovascular arteriosclerosis, hypertension, diabetic nephropathy, and congestive heart failure are longterm complications of the diabetic processes. Each of these disease states is accompanied by decreased enos activity, increased free radical generation, increased thrombogenic activity and therefore thrombotic and ischemic complications.

Second, since Rhamnan Sulphate is from plant cells, it has no potential for the transmission of potentially lethal and serious prion diseases such as mad cow disease.

Third, Rhamnan Sulphate has no potential for activating Platelet Factor IV and resulting in immune complex destruction of platelets as seen with heparin administration.

Fourth, Rhamnan Sulphate is a functional substitute for heparin in applications requiring systemic (not Plasma) anticoagulant activity such as dialysis, bypass surgery, and polymer tube coatings and devices for use in mammals and humans.

Fifth, the described composition has less peptide residues because it is extracted from plant cells as compared to heparin from animal cells. Hence, it is less allergic reaction prone and has fewer immunogenic properties.

It will be readily apparent to those skilled in the art that many modifications, derivations and improvements are within the scope of the invention. Such modifications, derivations, and improvements should be accorded full scope of protection by the claims appended hereto.

What is claimed is:

1. A method for treatment of Type II Diabetes Mellitus comprising the step of administering to a patient in need thereof a therapeutically-effective amount of Rhamnan Sulphate.

2. The method of claim 1 wherein anticoagulation activity in the blood plasma of a patient is not appreciably increased.

3. The method of claim 1 wherein the dose of Rhamnan Sulphate is equivalent to between approximately 5,000 IU and 20,000 IU of heparin activity on a daily basis.

4. The method of claim 1 wherein the dose of Rhamnan Sulphate is equivalent to between approximately 8,000 IU and 12,000 IU of heparin activity on a daily basis.

5. The method of claim 1 wherein the dose of Rhamnan Sulphate is approximately 7.5 mg/kg as a single dose.

6. The method of claim 1 wherein the dose of Rhamnan Sulphate is repeated daily.

7. The method of claim 1 further comprising the co-administration of L-Arginine.

8. The method of claim 1 wherein Type II Diabetes further comprises of complications selected from the group consisting of neuropathy, nephropathy, arteriosclerosis, and proteinuria.

9. The method of claim 1 wherein the Rhamnan Sulfate is administered to a human in conjunction with foods, drinks, health bars, bread or cereals.

10. A method of improving the structural integrity of islet cells for the treatment of Diabetes comprising the step of administering to a patient in need thereof an effective amount of Rhamnan Sulphate.

11. The method of claim 10 wherein anticoagulation activity in the blood plasma is not appreciably increased.

12. The method of claim 10 wherein the dose of Rhamnan Sulphate is equivalent to between approximately 2,000 IU and 200,000 IU of heparin activity daily.

13. The method of claim 10 wherein the dose of Rhamnan Sulphate is equivalent to between approximately 5,000 IU and 20,000 IU of heparin activity daily.

14. The method of claim 10 wherein the dose of Rhamnan Sulphate is equivalent to between approximately 8,000 IU and 12,000 IU of heparin activity daily.

15. The method of claim 10 wherein the dose of Rhamnan Sulphate is repeated daily.

16. The method of claim 10 further comprising the co-administration of L-Arginine.

17. The method of claim 10 wherein the structurally improved islet cells treat the onset of Type II Diabetes.

18. The method of claim 10 wherein the structurally improved islet cells treat the onset of neuropathy, nephropathy, arteriosclerosis, or proteinuria.

19. The method of claim 10 wherein the structurally improved islet cells treat the onset of thrombogenic activity.

* * * * *